(12) United States Patent
Ebara et al.

(10) Patent No.: US 9,079,008 B2
(45) Date of Patent: Jul. 14, 2015

(54) MEDICAL TUBE CLAMP

(75) Inventors: Yukinori Ebara, Osaka (JP); Kimihiko Nakamura, Osaka (JP); Akinobu Yamaguchi, Osaka (JP); Yasuki Tsuchitori, Osaka (JP)

(73) Assignee: NIPRO CORPORATION, Osaka (JP)

( * ) Notice: Subject to any disclaimer, the term of this patent is extended or adjusted under 35 U.S.C. 154(b) by 21 days.

(21) Appl. No.: 13/982,334

(22) PCT Filed: Feb. 14, 2012

(86) PCT No.: PCT/JP2012/000955
§ 371 (c)(1),
(2), (4) Date: Aug. 6, 2013

(87) PCT Pub. No.: WO2012/111310
PCT Pub. Date: Aug. 23, 2012

(65) Prior Publication Data
US 2013/0310768 A1 Nov. 21, 2013

(30) Foreign Application Priority Data
Feb. 17, 2011 (JP) .................. 2011-031920

(51) Int. Cl.
*A61M 39/28* (2006.01)
*A61M 5/168* (2006.01)

(52) U.S. Cl.
CPC ............. *A61M 39/284* (2013.01); *A61M 5/168* (2013.01); *A61M 5/16813* (2013.01); *A61M 39/28* (2013.01)

(58) Field of Classification Search
CPC .................................................. A61M 39/284

USPC ..................... 604/250; 251/4, 9, 10
See application file for complete search history.

(56) References Cited

U.S. PATENT DOCUMENTS

| 4,429,852 A | 2/1984 | Tersteegen et al. |
| 5,203,056 A | 4/1993 | Funk et al. |

(Continued)

FOREIGN PATENT DOCUMENTS

| JP | U-3-54654 | 5/1991 |
| JP | A-5-329210 | 12/1993 |

(Continued)

OTHER PUBLICATIONS

International Search Report issued in International Patent Application No. PCT/JP2012/000955 dated May 22, 2012.

(Continued)

*Primary Examiner* — Nicholas Lucchesi
*Assistant Examiner* — Anh Bui
(74) *Attorney, Agent, or Firm* — Oliff PLC (57) ABSTRACT

A medical tube clamp wherein first and second plate parts including, on opposing surfaces, compressive protrusions for closing a medical tube are provided with a pair of side walls on both sides projecting from one toward an other of the plate parts, and are also provided with a central guide protrusion projecting from the other toward the one of the plate parts. Both sides of a tip portion of the central guide protrusion make sloping guide surfaces projecting toward a center. When the plate parts are displaced relative to each other so as to become closer, lateral displacement of them is corrected by a slide of the pair of side walls and the sloping guide surfaces, and the central guide protrusion is inserted between the pair of side walls.

6 Claims, 5 Drawing Sheets

(56) References Cited

U.S. PATENT DOCUMENTS

2010/0152681 A1* 6/2010 Mathias .................. 604/250
2012/0232497 A1* 9/2012 Singh ..................... 604/250

FOREIGN PATENT DOCUMENTS

| JP | A-2000-88120 | 3/2000 |
| JP | A-2001-259030 | 9/2001 |
| JP | A-2003-235971 | 8/2003 |
| JP | A-2005-169146 | 6/2005 |
| JP | H-3113460 | 9/2005 |
| JP | U-3113762 | 9/2005 |

OTHER PUBLICATIONS

Oct. 31, 2014 Office Action issued in Chinese Patent Application No. 201280009329.3.

* cited by examiner

MEDICAL TUBE CLAMP

TECHNICAL FIELD

The present invention relates to a medical tube clamp applied to a flexible medical tube used for medical procedures wherein the tube is switched between a connected state and a shutoff state.

BACKGROUND ART

Conventionally in the medical field, a flexible medical tube has been used as a pipe constituting an extracorporeal circulation circuit or an auxiliary circuit for body fluid such as blood or a transfusion line of drug solution and the like. Also, a clamp device made of resin moldings has been used so as to make the medical tube closable at a desired position as needed.

Such a clamp device, as shown in Unexamined Japanese Patent Application Publication No. JP-A-2003-235971 (Patent Document 1), has a structure where a first plate part and a second plate part connected at a curved portion and each provided with a compressive protrusion on each opposing surface. Then, the medical tube is retained in a closed state being compressed between the compressive protrusions by the elastic deformation of the curved portion to lock the first and second plate parts at a location close to each other.

Meanwhile, it often requires promptness and reliability in the medical practice to switch the medical tube between a connected state and a shutoff state.

However, using the conventional clamp device, the medical tube is displaced off to the side from the compressive protrusions to pose a risk of incomplete shutoff, which used to require a careful handling.

In order to prevent the medical tube from being displaced off to the side, one option is to form a pair of side walls on both sides of one of the first and second plate parts in the width direction to prevent the displacement. However, once the pair of side walls are formed to prevent the displacement, relative displacement between the first and second plate parts in the direction of bringing them closer to each other is interfered by the compressive protrusion of the other plate part abutting against the end surfaces of the pair of side walls during the compressive operation of the medical tube, posing a risk of detrimental impact on the prompt closing operation of the medical tube.

BACKGROUND ART DOCUMENTS

Patent Documents

Patent Document 1: JP-A-2003-235971

SUMMARY OF THE INVENTION

Problem the Invention Attempts to Solve

The present invention was made against the background described above, and the problem to be solved thereby is to provide a medical tube clamp having a novel structure which is capable of promptly and reliably carrying out operations to close a medical tube by compression between compressive protrusions by means of relatively displacing the first and second plate parts in the direction of bringing them closer to each other while effectively preventing any relative positional displacement of the first and second plate parts to the sides as well as any displacement of the medical tube to the side relative to both of said plate parts.

Means for Solving the Problem

A first mode of the present invention provides a medical tube clamp comprising: a first plate part and a second plate part connected at a curved portion; compressive protrusions provided on opposing surfaces of the first plate part and the second plate part that close a medical tube by compression between them; and a locking member that elastically deforms the curved portion and retains the medical tube in a closed state by locking the first and second plate parts at a location close to each other, the medical tube clamp being characterized in that at least one of the first plate part and the second plate part has a pair of side walls on both sides that protrude out toward an other of the first plate part and the second plate part, in order to prevent the medical tube from being displaced off sideways, the other of the first plate part and the second plate part has a central guide protrusion that protrudes out toward the one of the first plate part and the second plate part, and both sides of a tip portion of the central guide protrusion protrude out toward a center to make sloping guide surfaces that guide the central guide protrusion into a gap between the pair of side walls while preventing interference against the pair of side walls during a relative displacement of the first and second plate parts in a direction of bringing them closer to each other.

In the present mode, since the medical tube is prevented from being displaced off sideways by the pair of side walls during the operation to close the medical tube, it is made possible to securely compress and close the medical tube between the compressive protrusions of the both plate parts. In addition, even when the two plate parts are displaced to the side relative to each other, the relative displacement to the side is corrected and the interference is prevented by the guiding action based on the abutting and sliding of the sloping guide surface against the pair of side walls to bring the first and second plate parts closer to each other to the original opposing position. As a result, it is possible to compress and close the medical tube securely and promptly between the compressive protrusions of the two plate parts.

A second mode of the present invention provides the medical tube clamp according to the first mode, wherein the pair of side walls as well as the central guide protrusion are formed on an opening side opposite the curved portion relative to the compressive protrusions.

In the present mode, the effects of correcting the relative displacement of the first and second plate parts to the side and preventing the interference based on the guiding action by the sliding between the sloping guide surfaces and the pair of side walls are exerted more effectively. In other words, since the relative displacement to the side of the first and second plate parts occurs centered around the curved portion side, it is effective to provide the sloping guide surfaces and the pair of side walls on the opening side where the relative displacement to the side is larger than the curved portion side.

A third mode of the present invention provides the medical tube clamp according to the first or second mode, wherein an engagement prevention protrusion is formed to protrude out from a top of the sloping guide surfaces toward the one of the first plate part and the second plate part, at the tip portion of the central guide protrusion.

In the present mode, the engagement prevention protrusion is provided at the position where the first and second plate parts open up as if opening its mouth between the edges on the opening side opposite the curved portion. This is effective to prevent any ingress of foreign matters into the opening. Therefore, the engagement prevention protrusion is able to avoid the problem that when many clamps are stored in a box or the like, plate parts of other clamps get into the opening between the first and second plate parts and makes it difficult to disentangle multiple clamps.

A fourth mode of the present invention provides the medical tube clamp according to any one of the first to third modes, wherein the one of the first plate part and the second plate part has a locking plate part rising up from an edge on the opening side opposite the curved portion toward the other of the first plate part and the second plate part, and the other of the first plate part and the second plate part is made lockable to the locking plate part, thereby constituting the locking member.

The present mode, favorably adopted especially when combined with the above third mode, is able to further reduce the size of the opening between the first and second plate parts on the opening side by a locking plate part provided on the one of the first and second plate parts and the engagement prevention protrusion provided on the other.

A fifth mode of the present invention provides the medical tube clamp according to any one of the first to fourth modes, wherein both of the first plate part and the second plate part have the pair of side walls, respectively, and one of the two pairs of side walls are formed on a side of the curved portion relative to the compressive protrusions whereas an other of the two pairs of side walls are provided on the opening side opposite the curved portion relative to the compressive protrusions.

In the present mode, since sideways displacement of the medical tube is prevented more effectively by the pair of side walls formed on both the curved side and opening side of the compressive protrusions, and the two pairs of side walls are formed offset from the compressive protrusions, it is easy to visually confirm the compressive closure of the medical tube by the compressive protrusions.

Effect of the Invention

Using the medical tube clamp of the present invention in the operation of closing the medical tube, sideways displacement of the medical tube is prevented by the pair of side walls on both sides and the medical tube is securely compressed and closed between the compressive protrusions. Also, by virtue of the guiding actions of the sloping guide surfaces and the pair of side walls, it is possible to promptly compress and close the medical tube between the compressive protrusions by bringing the plate parts closer to each other while preventing the interference due to lateral displacement of the first and second plate parts from each other.

EMBODIMENTS FOR CARRYING OUT THE INVENTION

Figure 5:
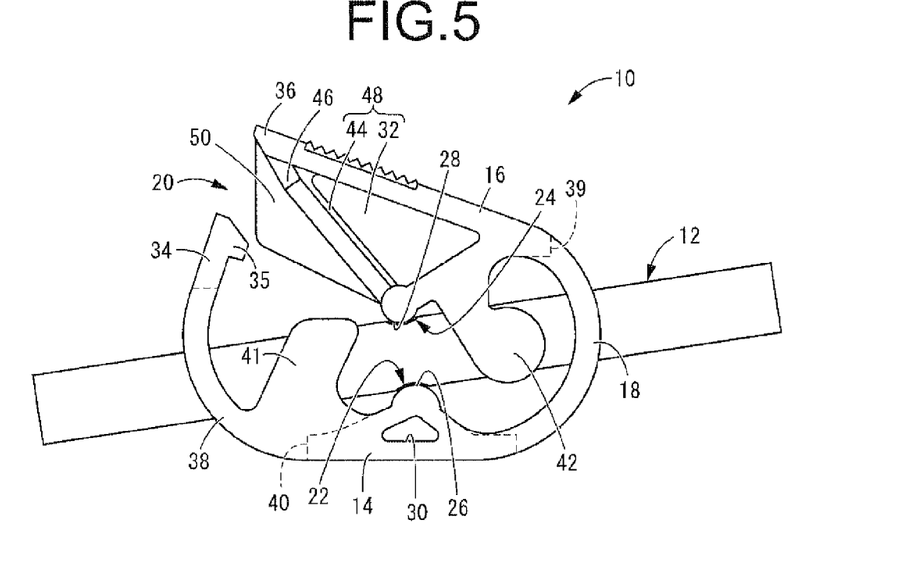
FIG. 5 is a side view of a mounted state of the medical tube clamp shown in FIG. 1 to a medical tube.
Figure 6:
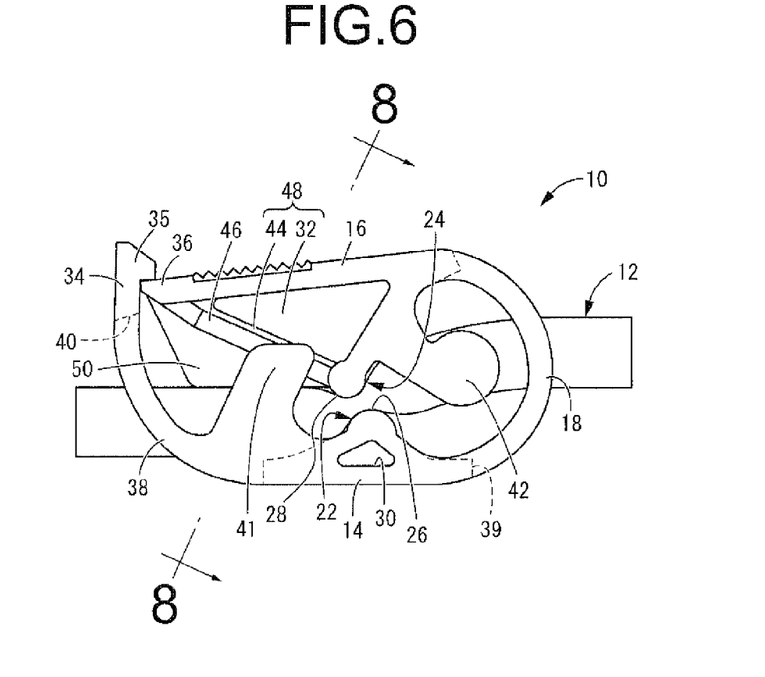
FIG. 6 is a side view of a closed state of the medical tube by the medical tube clamp shown in FIG. 5.
Figure 7:
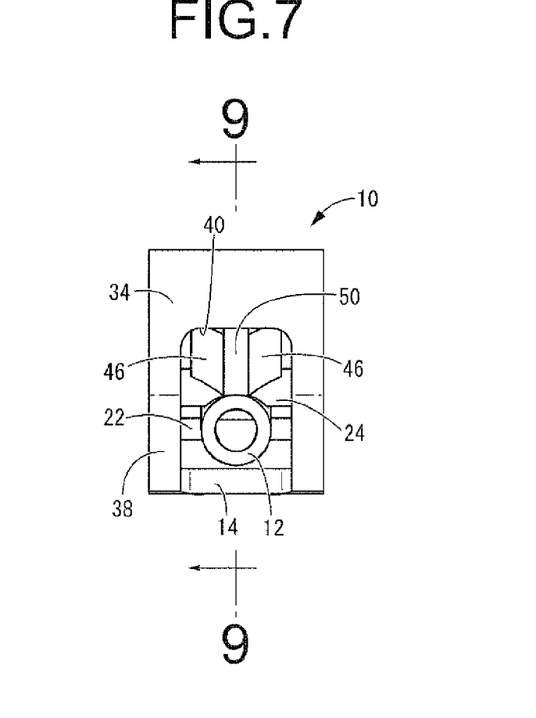
FIG. 7 is a front view of the closed state of the medical tube by the medical tube clamp shown in FIG. 6.
Figure 8:
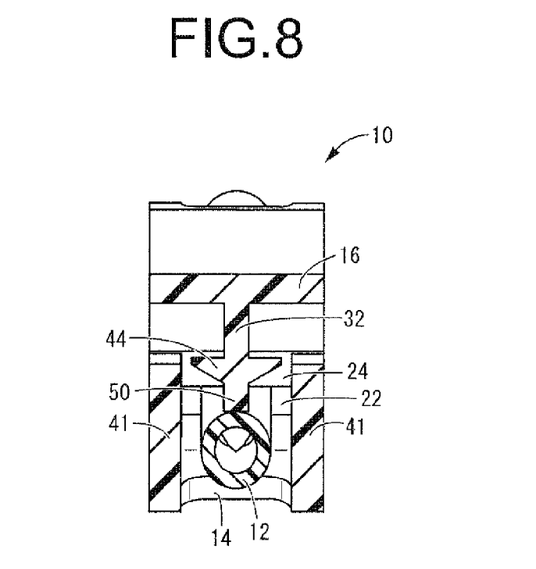
FIG. 8 is a cross-section taken along line 8-8 of FIG. 6.
Figure 9:
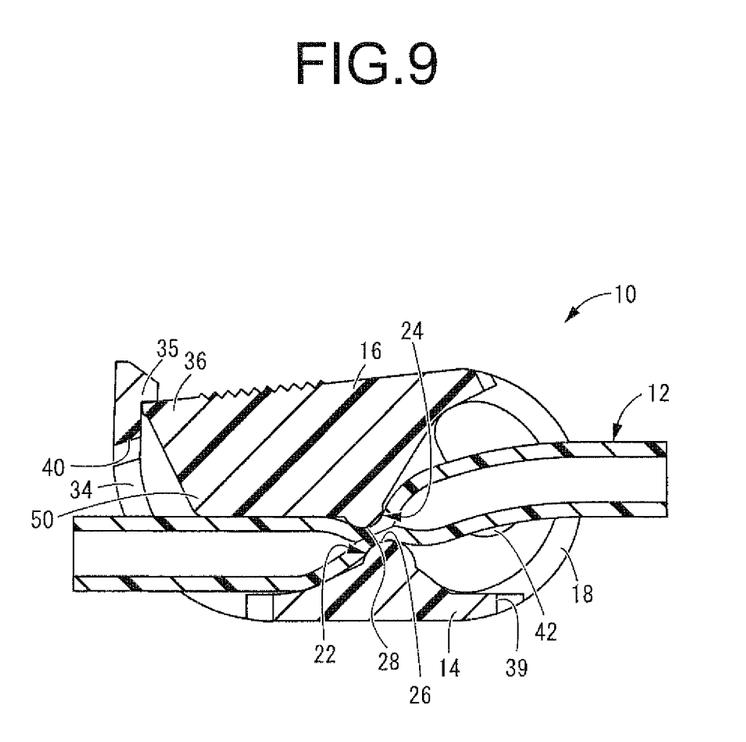
FIG. 9 is a cross-section taken along line 9-9 of FIG. 7.

FIGS. 1 to 4 show a medical tube clamp 10 as one embodiment of the present invention. The clamp 10 is integrally formed with a synthetic resin material and used in a state of being mounted to a flexible medical tube 12 that constitutes blood and liquid transfusion lines, as shown in FIG. 5, in order to retain the medical tube 12 compressed and closed as needed, as shown in FIGS. 6 to 9.

Figure 2:
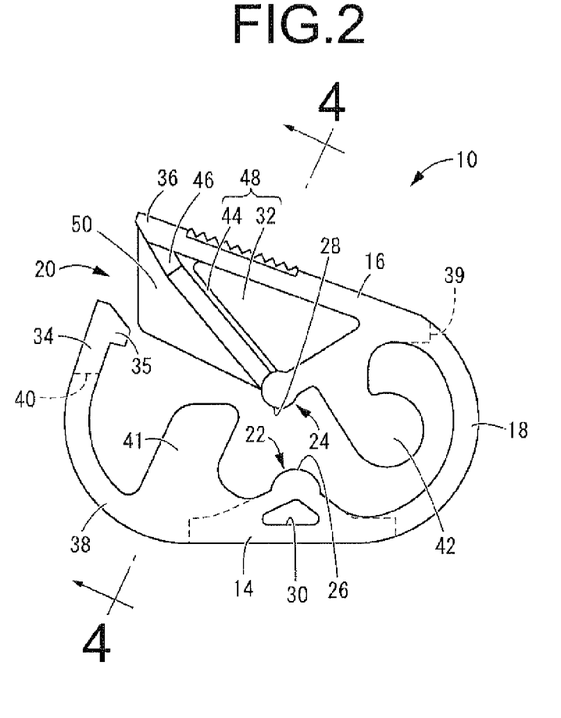
FIG. 2 is a side view of the medical tube clamp shown in FIG. 1.
Figure 3:
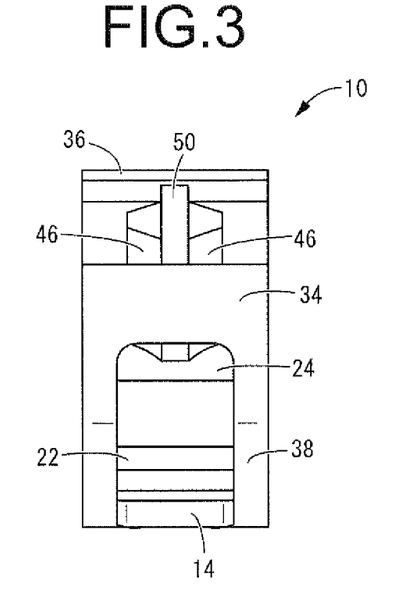
FIG. 3 is a front view of the medical tube clamp shown in FIG. 1.
Figure 4:
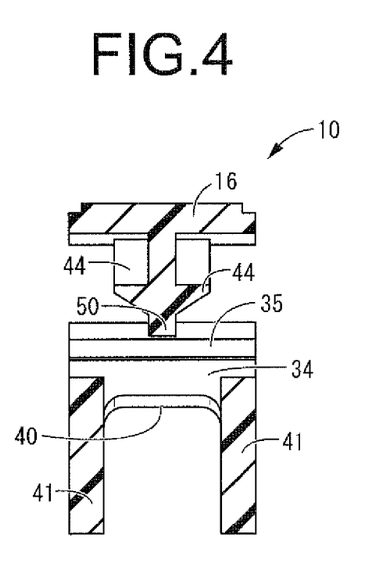
FIG. 4 is a cross-section taken along line 4-4 of FIG. 2.

More specifically, the clamp 10 comprises a first plate part 14 and a second plate part 16 each in an approximate shape of a flat plate, and the two plate parts 14, 16 are connected by a curved portion 18 at one end in the length direction thereof (left-right direction in FIG. 2). The first and second plate parts 14, 16 connected by the curved portion 18 are positioned opposite to each other keeping a given distance in between in the up-down direction of FIG. 2 slightly extending toward the other end thereof in the length direction. Then, on the other end side of the first and second plate parts 14, 16 in the length direction, an opening 20 is provided that opens up the area between the opposing faces of the two plate parts 14, 16 toward the outside.

Also, a first compressive protrusion 22 is formed in the middle of the first plate part 14 in the length direction protruding out toward the opposing face of the second plate part 16. Meanwhile, a second compressive protrusion 24 is formed in the middle of the second plate part 16 in the length direction protruding out toward the opposing face of the first plate part 14.

The first compressive protrusion 22 with a mound-shaped cross section extends across the width of the first plate part 14 and its tip portion is made to be a pressing surface 26 in a circular arc shape. The second compressive protrusion 24, made in a shape of a plate protruding out obliquely toward the opening 20, extends across the width of the second plate part 16, and its tip portion is made to be a pressing surface 28 in a circular arc shape. The pressing surfaces 26 and 28 of the first and second compressive protrusions 22 and 24, respectively, are positioned face-to-face with a given distance to each other as shown in FIG. 5.

The first compressive protrusion 22 is formed with lightening holes 30, 30 that open up at both ends in the width direction. Meanwhile, the second compressive protrusion 24 is formed with a reinforcing rib 32 in a shape of a triangle plate extending from the middle of the width direction thereof toward the opening 20.

Furthermore, the first plate part 14 is provided with a locking plate part 34 that rises up from the tip portion on the opening 20 side toward the second plate part 16. At the tip of the locking plate part 34, a locking pawl 35 is formed protruding inward and is positioned to face the tip portion of the second plate part 16 with a given distance across the opening 20 so as to constitute a locking member.

In other words, as shown in FIGS. 6 to 9, a tip portion 36 of the second plate part 16 can be positioned on the inner side of the locking plate part 34 after overriding the locking pawl 35 by means of elastically deforming the curved portion 18 to let the first and second plate parts 14 and 16 displace in the direction of getting closer to each other. Also, by having the tip portion 36 of the second plate part 16 locked by the locking pawl 35, relative displacement of the first and second plate parts 14 and 16 in the restoring direction of getting away from each other can be prevented. On the other hand, by deforming the locking plate part 34 outward to release the engagement of the locking pawl 35, the first and second plate parts 14 and 16 can return to their initial positions away from each other, as shown in FIG. 5, by virtue of the elasticity of the curved portion 18.

The locking plate part 34 is made in such a way that a base portion 38 of the first plate part 14 rising therefrom is curved in a shape of a circular arc plate to distribute the elastic stress and strain thereof. Also, through the curved portion 18 and the base portion 38 of the locking plate part 34 positioned face-to-face in the length direction of the first and second plate parts 14 and 16, through holes 39 and 40 are formed penetrating through from the inside out in the middle of the width direction. Then, by inserting the medical tube 12 into these through holes 39 and 40, the medical tube 12 is arranged to penetrate through the area between the opposing faces of the first and second plate parts 14 and 16.

In addition, by forming the through holes 39, 40 at the curved portion 18 and the base portion 38 of the locking plate part 34, the curved portion 18 and the base portion 38 of the locking plate part 34 can be elastically deformed more easily than the first and second plate parts 14 and 16.

Also, in the present embodiment, one of the plate parts, that is, the first plate part 14 is foamed with a pair of first side walls 41, 41 on both sides located on the opening 20 side relative to the first compressive protrusion 22 protruding out toward the second plate part 16 on both sides in the width direction. The pair of first side walls 41, 41 are formed with a protrusion larger than that of the first compressive protrusion 22 and less than reaching the second plate part 16 at a relatively close-in position between the first and second plate parts 14 and 16. The pair of first side walls 41, 41 are made in an approximate shape of a flat plate with an approximately flat surface at the protruded tip.

Meanwhile, in the present embodiment, the other plate part, that is, the second plate part 16 is formed with a pair of second side walls 42, 42 on both sides located on the curved portion 18 side relative to the second compressive protrusion 24 protruding out toward the first plate part 14 on both sides in the width direction. The pair of second side walls 42, 42 are sloping toward the curved portion 18 from both ends in the width direction from the middle position in the height direction of the second compressive protrusion 24 in a plate shape protruding out obliquely toward the opening 20 so as to protrude out toward the first plate part 14. The pair of second side walls 42, 42 are formed with a protrusion larger than that of the second compressive protrusion 24 and less than reaching the first plate part 14 at a relatively close-in position between the first and second plate parts 14 and 16. The pair of second side walls 42, 42 are in an approximate shape of a flat plate.

In addition, the second plate part 16 is made in such a way that the reinforcing rib 32 protrudes out toward the first plate part 14 in the middle in the width direction of the second plate part 16 on the opening 20 side relative to the pressing surface 28 of the second compressive protrusion 24. The protruding tip of the reinforcing rib 32 slopes down from the tip portion of the second compressive protrusion 24 toward the opening 20 to gradually reduce its height. On the sloping protrusion of the tip portion of the reinforcing rib 32, sloping plates 44, 44 are provided protruding out toward both sides in the direction of the rib thickness.

Such sloping plates 44, 44 are made with a protrusion height less than that of the pair of first side walls 41, 41 of the first plate part 14. And, as shown in FIGS. 6 to 9, the sloping plates 44, 44 enter into the space between the pair of first side walls 41, 41 of the first plate part 14 when the first and second plate parts 14 and 16 are displaced in the direction of getting closer to each other.

Also, the surfaces of the sloping plates 44, 44 facing the first plate part 14 are made to be sloping guide surfaces 46, 46 that slope in the direction of getting closer to the second plate part 16 as they extend outward on both sides from the reinforcing rib 32. In other words, the sloping guide surfaces 46, 46 slope down toward the center from both sides in the width direction of the second plate part 16.

And in the present embodiment, a central guide protrusion 48 is configured with the reinforcing rib 32 and the sloping plates 44, 44, and when the first and second plate parts 14 and 16 are displaced in the direction of getting closer to each other, the tip portion of the first side wall 41 hits against the sloping guide surface 46 of the sloping plate 44 when the two plate parts 14 and 16 are laterally displaced from each other. This hitting allows the tip portions of the pair of first side walls 41, 41 to be guided along the sloping guide surfaces 46, 46 on both sides of the tip portion of the central guide protrusion 48 to prevent a catch against the tip portions of the pair of first side walls 41, 41, and lateral displacement of the first and second plate parts 14 and 16 from each other is corrected as the first and second plate parts 14 and 16 are relatively displaced in the direction of getting further closer to each other.

As a result, as ultimately shown in FIGS. 6 to 9, the sloping plates 44, 44 of the second plate part 16 enter into the pair of first side walls 41, 41 of the first plate part 14 while the tip portion 36 of the second plate part 16 is locked and retained by the locking pawl 35 of the locking plate part 34 with the first and second plate parts 14 and 16 facing close to each other at their proper locations.

Furthermore, an engagement prevention protrusion 50 protruding out toward the first plate part 14 is formed at the protruded tip of the central guide protrusion 48 on the second plate part 16. This engagement prevention protrusion 50, made in a shape of a flat plate, protrudes out from the apex of the sloping guide surfaces 46, 46 of the sloping plates 44, 44, extending along the edge at the tip of the central guide protrusion 48. The protrusion height of the engagement prevention protrusion 50 from the second plate part 16 is preferably made equal or slightly larger than the separation distance between the second plate part 16 and the locking plate part 34 at the tip on the side of the opening 20.

Figure 1:
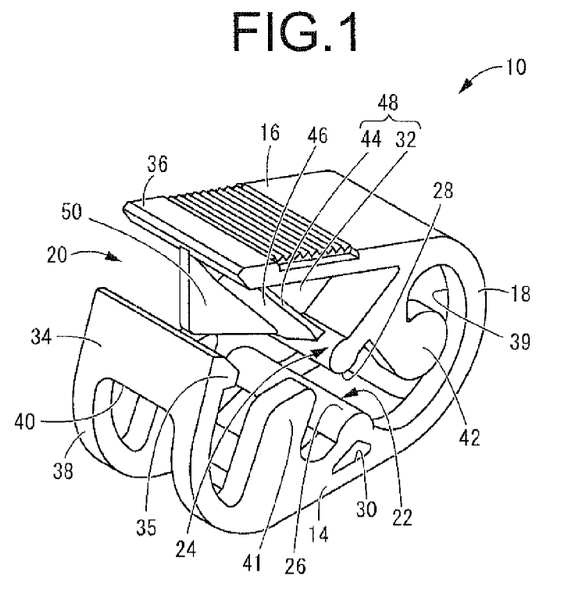
FIG. 1 is a perspective view of a medical tube clamp as one embodiment of the present invention.

The clamp 10 structured as described above is shipped out in the condition shown in FIG. 1, but even when a plurality of them are packed in one container such as a bag or a box during the handling thereof, the problem can be prevented that the first and second plate parts 14 and 16 or the locking plate part 34 of other clamps 10 get stuck in the opening 20 to make it difficult to disengage them because the engagement prevention protrusion 50 is provided to stay in the opening 20.

Then, such clamp 10, as shown in FIG. 5, is used under a condition of externally attached to the medical tube 12 in the medical practice, but under such a condition, the medical tube 12 is inserted through the through holes 39, 40 of the curved portion 18 and the locking plate part 34, respectively, and sideways displacement of the medical tube 12 is prevented by each pair of the first and second side walls 41, 42. Therefore, the medical tube 12 is stably maintained in a condition of being penetrated through the area between the opposing surfaces of the first and second plate parts 14 and 16.

Furthermore, under the fitted condition of the medical tube 12, the first and second plate parts 14 and 16 can be retained in a close-in position by means of pinching and pressing each outer face of the first and second plate parts 14 and 16 with fingers in the direction of bringing them closer to each other and having the second plate part 16 locked against the locking plate part 34. This allows, as shown in FIGS. 6 to 9, the first and second compressive protrusions 22 and 24 to be pressed against the medical tube 12 from both sides. The distance between the opposing faces of the first and second compressive protrusions 22 and 24 is made smaller than the wall thickness of the medical tube 12, which causes the medical tube 12 to be fully crushed between the compressive protrusions 22, 24 and retained in a closed condition to shut off the inner channel.

Thus, in the course of pressing the first and second compressive protrusions 22 and 24 against the medical tube 12 so as to change its inner channel from an open state to closed state, the medical tube 12 can be securely closed because sideways displacement of the medical tube 12 is prevented by each pair of the first and second side walls 41, 42 in addition to the through holes 39, 40 of the curved portion 18 and the locking plate part 34, respectively.

Especially in the present embodiment, the first and second compressive protrusions 22 and 24 are positioned slightly off from each other in the length direction of the medical tube 12, and the medical tube 12 compressed between these compressive protrusions 22, 24 is displaced to the side of the second plate part 16 on the side of the curved portion 18 from the compressed portion, whereas it is displaced to the side of the first plate part 14 on the opening 20 side from the compressed portion. Therefore, on the side of the curved portion 18 from the compressed portions, the effect of preventing the displacement by the pair of second side walls 42, 42 installed to protrude out from the second plate part 16 is exerted more effectively, whereas, on the side of the opening 20 from the compressed portions, the same effect by the pair of first side walls 41, 41 installed to protrude out from the first plate part 14 is also exerted more effectively.

Also, since the pair of first side walls 41, 41 and pair of second side walls 42, 42 are installed at positions off to the sides from the portion of the medical tube 12 compressed by the first and second compressive protrusions 22 and 24, the state of compression of the medical tube 12 can easily be confirmed visually from outside.

The present invention is not limited to the specific descriptions of the above embodiment. For example, in the embodiment described above, the entire clamp was integrally formed with a synthetic resin material, but it is also possible to form a clamp with a divided structure where a plurality of members are fixed to each other. Also, specific shapes of the first and second compressive protrusions 22 and 24 as well as the first and second side walls 41 and 42 and so forth can be set arbitrarily. Furthermore, in the present embodiment, as a pair of side walls that prevent sideways displacement of the medical tube 12 during the closing operation of the clamp, the pair of first side walls 41, 41 can be provided to follow the guidance of the sloping guide surfaces 46, 46 of the central guide protrusion 48, and the pair of second side walls 42, 42 are not necessarily essential. Moreover, the position to install the locking member is not limited to the opening 20 side.

Keys to Symbols

10: Medical tube clamp, 12: Medical tube, 14: First plate part, 16: Second plate part, 18: Curved portion, 20: Opening, 22: First compressive protrusion, 24: Second compressive protrusion, 34: Locking plate part, 41: First side wall, 42: Second side wall, 46: Sloping guide surface, 48: Central guide protrusion, 50: Engagement prevention protrusion

The invention claimed is:

1. A medical tube clamp comprising:
a first plate part and a second plate part connected at a curved portion at one end in a length direction of each of the first and second plate parts;
compressive protrusions provided on opposing surfaces of the first plate part and the second plate part that close a medical tube by compression between them; and
a locking member that elastically deforms the curved portion and retains the medical tube in a closed state by locking the first and second plate parts at a location close to each other,
wherein at least one of the first plate part and the second plate part has a pair of side walls provided on both sides in a width direction of the opposing surface with a gap therebetween that protrude out toward an other of the first plate part and the second plate part, in order to prevent the medical tube from being displaced off sideways, the pair of side walls being separate from the compressive protrusions,
the other of the first plate part and the second plate part has a central guide protrusion that protrudes out toward the one of the first plate part and the second plate part,
both sides of a tip portion of the central guide protrusion protrude out toward a center to make sloping guide surfaces that guide the central guide protrusion into the gap between the pair of side walls while preventing interference against the pair of side walls during a relative displacement of the first and second plate parts in a direction of bringing them closer to each other, and
the sloping guide surfaces of the central guide protrusion have a size so that the sloping guide surfaces are housed within the gap between the pair of side walls in the width direction with an entire part of the sloping guide surfaces being spaced away from and being not held in contact with the pair of side walls.

2. The medical tube clamp according to claim 1, wherein the pair of side walls as well as the central guide protrusion are formed on an opening side opposite the curved portion relative to the compressive protrusions.

3. The medical tube clamp according to claim 1, wherein the one of the first plate part and the second plate part has a locking plate part rising up from an edge on an opening side opposite the curved portion toward the other of the first plate part and the second plate part, and the other of the first plate part and the second plate part is made lockable to the locking plate part, thereby constituting the locking member.

4. The medical tube clamp according to claim 1, wherein both of the first plate part and the second plate part have the pair of side walls, respectively, and one of the two pairs of side walls are formed on a side of the curved portion relative to the compressive protrusions whereas an other of the two pairs of side walls are provided on an opening side opposite the curved portion relative to the compressive protrusions.

5. The medical tube clamp according to claim 1, wherein the locking member locks other ends in the length direction of the first and second plate parts, and the locking member including a locking plate part, and the curved portion and the locking plate part are spaced away and positioned face-to-face in the length direction of the first and second plate parts, and a pair of through holes are formed penetrating through the curved portion and the locking plate part, respectively so that the medical tube is arranged to penetrate through the pair of through holes and through an area between the opposing surfaces of the first and second plate parts while extending in the length direction of the first and second plate parts.

6. A medical tube clamp comprising:
a first plate part and a second plate part connected at a curved portion at one end in a length direction of each of the first and second plate parts;

compressive protrusions provided on opposing surfaces of the first plate part and the second plate part that close a medical tube by compression between them;

a locking member that elastically deforms the curved portion and retains the medical tube in a closed state by locking the first and second plate parts at a location close to each other, wherein at least one of the first plate part and the second plate part has a pair of side walls provided on both sides in a width direction of the opposing surface with a gap therebetween that protrude out toward an other of the first plate part and the second plate part, in order to prevent the medical tube from being displaced off sideways, the pair of side walls being separate from the compressive protrusions, the other of the first plate part and the second plate part has a central guide protrusion that protrudes out toward the one of the first plate part and the second plate part, both sides of a tip portion of the central guide protrusion protrude out toward a center to make sloping guide surfaces that guide the central guide protrusion into the gap between the pair of side walls while preventing interference against the pair of side walls during a relative displacement of the first and second plate parts in a direction of bringing them closer to each other, and the sloping guide surface of the central guide protrusion have a size so that the sloping guide surfaces are housed within the gap between the pair of side walls in the width direction while being spaced away from the pair of side walls; and an engagement prevention protrusion formed to protrude out from a top of the sloping guide surfaces toward the one of the first plate part and the second plate part, at the tip portion of the central guide protrusion.

\* \* \* \* \*